(12) United States Patent
Ishii et al.

(10) Patent No.: US 7,271,285 B2
(45) Date of Patent: Sep. 18, 2007

(54) PROCESS FOR PRODUCING AROMATIC CARBOXYLIC ACIDS

(75) Inventors: Yasutaka Ishii, Takatsuki (JP); Tatsuya Nakano, Himeji (JP)

(73) Assignee: Daicel Chemical Industries Ltd., Sakai-Shi, Osaka (JP)

( * ) Notice: Subject to any disclaimer, the term of this patent is extended or adjusted under 35 U.S.C. 154(b) by 402 days.

(21) Appl. No.: 10/785,982

(22) Filed: Feb. 26, 2004

(65) Prior Publication Data
US 2004/0171871 A1    Sep. 2, 2004

(30) Foreign Application Priority Data
Feb. 27, 2003   (JP) .............................. 2003-051362

(51) Int. Cl.
*C07C 51/00* (2006.01)
*C07C 51/16* (2006.01)

(52) U.S. Cl. ...................................... 562/406; 562/412

(58) Field of Classification Search ................ 562/406, 562/412
See application file for complete search history.

(56) References Cited

U.S. PATENT DOCUMENTS

| | | | |
|---|---|---|---|
| 3,346,625 A | 10/1967 | Fenton et al. | |
| 3,920,734 A * | 11/1975 | Ichikawa et al. | ........... 562/406 |
| 3,923,883 A | 12/1975 | Gaenzler et al. | |
| 4,093,647 A | 6/1978 | van Venrooy | |
| 4,673,753 A | 6/1987 | Siedle | |
| 4,788,308 A | 11/1988 | Siedle | |
| 5,393,922 A | 2/1995 | Sen et al. | |
| 5,760,288 A * | 6/1998 | Asahi et al. | ................. 562/412 |

FOREIGN PATENT DOCUMENTS

| | | |
|---|---|---|
| GB | 1083880 A | 9/1967 |
| GB | 1183226 A | 3/1970 |
| GB | 1445116 A | 8/1973 |
| GB | 1435635 A | 5/1976 |
| WO | WO98/45038 A1 | 10/1998 |

OTHER PUBLICATIONS

Beilstein Institut zur Förderung der Chemischen Wissenschaften, Frankfurt am Main, DE retrieved from BEILSTEIN Database accession No. rid 3917848-XP002280650 * Abstract* & Kalinovskii, I.; Gel' Bshtein, A. and Pogorelov, V.: Russ. J. Gen. Chem., vol. 71, No. 9, pp. 1463-1466 (2001).

Beilstein Institut zur Förderung der Chemischen Wissenschaften, Frankfurt am Main, DE retrieved from BEILSTEIN Database accession No. rid 3917401—XP002280651 * Abstract* & Kalinovskii, I.; Lescheva, A., Kuteinikova, M. and Gel' Bshtein, A. and Pogorelov, V.: Russ., J. Gen. Chem., USSR, EN, vol. 60, No. 1-2, pp. 108-113 (1990).

* cited by examiner

*Primary Examiner*—Taylor Victor Oh
(74) *Attorney, Agent, or Firm*—Birch, Stewart, Kolasch & Birch, LLP

(57) ABSTRACT

An aromatic compound (C) is reacted with carbon monoxide (D) and molecular oxygen (E) in the presence of a palladium compound catalyst (A) and a catalyst (B) and thereby yields a aromatic carboxylic acid corresponding to the aromatic compound (C) except with one or more carboxyl groups bonded to its aromatic ring. The catalyst (B) contains a heteropolyacid or a salt thereof (B1) or a mixture of oxo acids and/or salts thereof (B2), and the mixture (B2) contains, as a whole, one of P and Si and at least one selected from V, Mo and W.

3 Claims, No Drawings

PROCESS FOR PRODUCING AROMATIC CARBOXYLIC ACIDS

This Non-provisional application claims priority under 35 U.S.C. § 119(a) on Patent Application No(s). 2003-051362 filed in Japan on Feb. 27, 2003, the entire contents of which are hereby incorporated by reference.

BACKGROUND OF THE INVENTION

1. Field of the Invention

The present invention relates to a process for producing an aromatic carboxylic acid. More specifically, it relates to a process for producing a corresponding aromatic carboxylic acid by oxidative carboxylation of an aromatic compound using carbon monoxide and oxygen. Such aromatic carboxylic acids are useful as raw materials for polymers, intermediates for the synthesis of fine chemicals such as dyes and pharmaceutical preparations, and intermediates for other organic chemicals.

2. Description of the Related Art

Certain aromatic carboxylic acids have been prepared by oxidative carboxylation of an aromatic compound using carbon monoxide by catalysis of a divalent palladium. As such oxidative carboxylation, one using $K_2S_2O_8$ as an oxidizing agent has been reported (Synlett, 1996, 591-599). However, this technique using $K_2S_2O_8$ as an oxidizing agent requires a complicated aftertreatment, invites high cost and applies heavy loads to the environment.

SUMMARY OF THE INVENTION

Accordingly, an object of the present invention is to provide a process for producing an aromatic carboxylic acid from a corresponding aromatic compound using an oxidizing agent which is inexpensive, can be handled easily and applies less loads to the environment.

After intensive investigations to achieve the above object, the present inventors have found that an aromatic carboxylic acid can be efficiently produced from a corresponding aromatic compound, carbon monoxide and oxygen by using a palladium compound in combination with a specific catalyst. The present invention has been accomplished based on these findings.

Specifically, the present invention provides a process for producing an aromatic carboxylic acid, including the step of reacting an aromatic compound (C) with carbon monoxide (D) and molecular oxygen (E) in the presence of a palladium compound catalyst (A) and a catalyst (B) to thereby yield an aromatic carboxylic acid corresponding to the aromatic compound (C), except with one or more carboxyl groups bonded to its aromatic ring, the catalyst (B) containing a heteropolyacid or a salt thereof (B1) and/or a mixture of oxo acids and/or salts thereof (B2), the mixture (B2) containing, as a whole, one of P and Si and at least one selected from V, Mo and W.

The heteropolyacid or a salt thereof (B1) may contain, as its constitutional elements, one of P and Si and at least one selected from V, Mo and W. The heteropolyacid or a salt thereof (B1) may be a phosphovanadomolybdic acid or phosphomolybdic acid represented by the following formula:

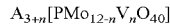

$$A_{3+n}[PMo_{12-n}V_nO_{40}]$$

wherein A represents at least one selected from the group consisting of hydrogen atom, $NH_4$, an alkali metal and an alkaline earth metal; and n is an integer from 0 to 10, or a salt of them.

The process of the present invention uses a palladium compound in combination with a specific compound as catalysts and can thereby efficiently produce an aromatic carboxylic acid from a corresponding aromatic compound using carbon monoxide and oxygen under mild conditions. The process exhibits good handleability and operability and can produce the target compound at low cost with a simple aftertreatment with less loads to the environment.

The term "palladium compound" as used herein also includes elementary palladium.

Further objects, features and advantages of the present invention will become apparent from the following description of the preferred embodiments.

DESCRIPTION OF THE PREFERRED EMBODIMENTS

Catalysts

The process of the present invention uses, as catalysts, a palladium compound catalyst (A) and a catalyst (B) comprising heteropolyacid or a salt thereof (B1) or a mixture of oxo acids and/or salts thereof (B2) containing one of P and Si and at least one selected from V, Mo and W.

Examples of the palladium compound catalyst (A) are metal palladium, zerovalent palladium complexes, and other zerovalent palladium compounds; palladium(II) acetate, palladium(II) cyanide, and other organic acid salts of divalent palladium, bis(acetylacetonato)palladium(II), dichlorobis(benzonitrile)palladium(II), and other organic complexes of divalent palladium, palladium(II) fluoride, palladium(II) chloride, palladium(II) bromide, palladium(II) iodide, and other halides of divalent palladium, palladium(II) nitrate, palladium(II) sulfate, and other oxoacid salts of divalent palladium, palladium(II) oxide, palladium(II) sulfide, palladium(II) selenide, palladium(II) hydroxide, tetraamminepalladium(II) chloride, other inorganic complexes of divalent palladium, and other divalent palladium compounds.

Among these palladium compounds, preferred are palladium(II) acetate, and other organic acid salts and organic complexes of divalent palladium, palladium(II) chloride and other halides of divalent palladium, palladium(II) sulfate, other oxoacid salts of divalent palladium, and other divalent palladium compounds.

The palladium compounds can be used as supported catalysts supported on a carrier such as active carbon, silica, alumina or zeolite. A naturally occurring mineral, such as hydrotalcite or hydroxyapatite, incorporating with palladium as a constitutional element can also be used as the palladium compound. Each of the palladium compounds can be used alone or in combination.

The amount of the palladium compound(s) is, for example, from about 0.000001 to about 0.5 mole, preferably from about 0.0001 to about 0.2 mole, and more preferably from about 0.005 to about 0.1 mole per 1 mole of the material aromatic compound (C).

The heteropolyacid in the heteropolyacid or a salt thereof (B1) is a condensate of oxoacids containing two or more different central ions and also refers to a heteronuclear poly acid (heteronuclear condensed acid). The heteropolyacids each comprise, for example, an oxoacid ion of P, As, Sn, Si, Ti or Zr, such as phosphoric acid or silicic acid, and another oxoacid ion of V, Mo or W, such as vanadic acid, molybdic acid or tungstic acid. Combinations of these oxoacid ions can yield various types of heteropolyacids.

Heteroatoms of oxoacids constituting the heteropolyacids are not specifically limited and examples thereof are Cu, Be, B, Al, C, Si, Ge, Sn, Ti, Zr, Ce, Th, N, P, As, Sb, V, Nb, Ta, Cr, Mo, W, U, Se, Te, Mn, I, Fe, Co, Ni, Rh, Os, Ir and Pt. The heteropolyacids preferably each comprise at least one selected from P, Si, V, Mo and W. More preferably, they each comprise P and/or Si and at least one selected from V, Mo and W, and further preferably comprise P and/or Si and at least one of V and Mo.

Heteropoly-anions constituting the heteropolyacids and salts thereof may have various compositions. The heteropoly-anions preferably have a composition represented by: $XM_{12}O_{40}$, wherein X is an element such as Si or P; and M is another element such as Mo, W or V. Examples of heteropoly-anions having the composition are anions of phosphomolybdic acids, phosphotungstic acids, silicomolybdic acids, silicotungstic acids and phosphovanadomolybdic acids.

The heteropolyacid may be a free heteropolyacid or a salt of a heteropolyacid, except with another cation replacing at least a part of hydrogen atoms corresponding to the cation of the heteropolyacid. Such cations capable of replacing the hydrogen atoms include, but are not limited to, cations of ammonium such as $NH_4$; alkali metals such as Cs, Rb, K, Na and Li; and alkaline earth metals such as Ba, Sr, Ca and Mg.

Among these heteropolyacids and salts thereof, a phosphovanadomolybdic acid or phosphomolybdic acid represented by the following formula:

$$A_{3+n}[PMo_{12-n}V_nO_{40}]$$

wherein A is a heteropolyacid cation; and n is an integer from 0 to 10 and preferably from 1 to 10, or a salt thereof is preferably used.

Examples of the cation represented by A include hydrogen atom and the aforementioned cations. Among them, typically preferred are fully protic phosphovanadomolybdic acids and phosphomolybdic acids, as well as phosphovanadomolybdic acids and phosphomolybdic acids except with $NH_4$ replacing at least part of protons. Examples of such fully protic phosphovanadomolybdic acids are $H_4PMo_{11}VO_{40}$, $H_5PMo_{10}V_2O_{40}$, $H_6PMo_9V_3O_{40}$ and $H_7PMo_8V_4O_{40}$.

The heteropolyacid or a salt thereof may be anhydrous or may contain crystal water. It can be used as a supported catalyst supported by a carrier such as active carbon. In this case, the heteropolyacid or a salt thereof and the palladium compound may be dispersed in and supported by one carrier. Each of the heteropolyacids and salts thereof can be used alone or in combination.

The mixture (B2) of oxoacids and/or salts thereof for use in the present invention is not specifically limited as long as it is a mixture containing, as a whole, one of P and Si, and at least one selected from V, Mo, and W. The term "oxoacid" as used herein also includes heteropolyacids. In contrast, the term "oxoacid in the narrow sense" does not include such heteropolyacids.

Such heteropolyacids containing at least one of P, Si, V, Mo and W include, but are not limited to, phosphomolybdic acid, phosphotungstic acid, phosphovanadic acid, phosphovanadomolybdic acid, silicomolybdic acid, silicotungstic acid and silicovanadic acid. The oxoacids in the narrow sense containing one of P, Si, V, Mo and W include, but are not limited to, phosphoric acid, silicic acid, vanadic acid, molybdic acid and tungstic acid. Salts of these heteropolyacids and of oxoacids in the narrow sense include, for example, ammonium salts, alkali metal salts and alkaline earth metal salts.

The mixture (B2) of oxoacids and/or salts thereof may be, for example, (i) a mixture of two or more different heteropolyacids and/or salts thereof, such as a mixture of phosphomolybdic acid or a salt thereof with phosphovanadic acid or a salt thereof; (ii) a mixture of a heteropolyacid or a salt thereof with an oxoacid in the narrow sense or a salt thereof, such as a mixture of phosphomolybdic acid or a salt thereof with vanadic acid or a salt thereof, and a mixture of a phosphovanadic acid or a salt thereof with molybdic acid or a salt thereof; or (iii) a mixture of two or more different oxoacids in the narrow sense and/or salts thereof, such as a mixture of phosphoric acid or a salt thereof, molybdic acid or a salt thereof, and vanadic acid or a salt thereof. These oxoacids and salts thereof may be anhydrous or may contain crystal water.

The amount of the catalyst (B) is not specifically limited and is, for example, from about 0.00001 to about 0.5 mole, preferably from about 0.0001 to about 0.1 mole, and more preferably from about 0.001 to about 0.05 mole per 1 mole of the material aromatic compound (C).

Carbon Monoxide (D)

The carbon monoxide (D) is not specifically limited and may be pure carbon monoxide or carbon monoxide diluted with an inert gas such as nitrogen, helium or argon gas. Carbon monoxide formed in the reaction system can also be used.

The amount of the carbon monoxide (D) can be set depending on, for example, the type of the material aromatic compound (C) and is generally about 0.5 mole or more (e.g., about 1 mole or more), preferably from about 1 to about 100 moles, and more preferably from about 1 to about 50 moles per 1 mole of the aromatic compound (C).

Molecular Oxygen (E)

The molecular oxygen (E) is not specifically limited and can be any of, for example, pure oxygen, air and diluted oxygen with an inert gas such as nitrogen, helium or argon gas.

The amount of the molecular oxygen (E) is generally about 0.5 mole or more (e.g., about 1 mole or more), preferably from about 1 to about 100 moles, and more preferably from about 1 to about 50 moles per 1 mole of the material aromatic compound (C). The molecular oxygen (E) is often used in excess to the aromatic compound (C).

Aromatic Compound (C)

The aromatic compound (C) for use as the raw material in the present invention is not specifically limited, as long as it is a compound containing an aromatic ring having at least one moiety (e.g. a carbon-hydrogen bond) that can undergo oxidative carboxylation. The aromatic ring may be any of an aromatic hydrocarbon ring and an aromatic heterocyclic ring and may have one or more substituents within a range not adversely affecting the reaction.

The aromatic compound (C) is represented by, for example, following Formula (1):

$$Ar—H \quad (1)$$

wherein Ar is an aromatic cyclic group. In Formula (1), the aromatic cyclic group as Ar can be an aromatic hydrocarbon group or an aromatic heterocyclic group. The aromatic hydrocarbon ring in the aromatic hydrocarbon group and the aromatic heterocyclic ring in the aromatic heterocyclic group may have one or more substituents within a range not adversely affecting the reaction.

The aromatic hydrocarbon rings include, for example, benzene ring; condensed carbon rings such as naphthalene, azulene, indacene, anthracene, phenanthrene, triphenylene, pyrene, and other condensed carbon rings each comprising two to ten 4- to 7-membered carbon rings condensed with each other.

Examples of the heterocyclic ring are heterocyclic rings each containing at least one oxygen atom as a heteroatom, such as furan, oxazole, isoxazole and other 5-membered rings, 4-oxo-4H-pyran and other 6-membered rings, benzofuran, isobenzofuran, 4-oxo-4H-chromene and other condensed rings; heterocyclic rings each containing at least one sulfur atom as a heteroatom, such as thiophene, thiazole, isothiazole, thiadiazole and other 5-membered rings, 4-oxo-4H-thiopyran and other 6-membered rings, benzothiophene and other condensed rings; heterocyclic rings each containing at least one nitrogen atom as a heteroatom, such as pyrrole, pyrazole, imidazole, triazole and other 5-membered rings, pyridine, pyridazine, pyrimidine, pyrazine and other 6-membered rings, indole, quinoline, acridine, naphthyridine, quinazoline, purine and other condensed rings.

Examples of substituents which the aromatic rings (the aromatic hydrocarbon rings and aromatic heterocyclic rings) may have are alkyl groups such as methyl, ethyl, isopropyl, t-butyl, and other $C_1$-$C_4$ alkyl groups; alkenyl groups such as vinyl, allyl and other $C_1$-$C_4$ alkenyl groups; alkynyl groups; alicyclic hydrocarbon groups; aromatic hydrocarbon groups such as phenyl and naphthyl groups; acyl groups; heterocyclic groups; halogen atoms; hydroxyl group; mercapto group; substituted oxy groups such as methoxy group, other $C_1$-$C_4$ alkoxy groups and other alkoxy groups, phenoxy group and other aryloxy groups, acetyloxy group and other acyloxy groups; substituted thio groups; carboxyl group; substituted oxycarbonyl groups such as methoxycarbonyl, ethoxycarbonyl, other $C_1$-$C_4$ alkoxy-carbonyl groups, and other alkoxycarbonyl groups; substituted or unsubstituted carbamoyl groups; cyano group; nitro group; substituted or unsubstituted amino groups such as amino group, N,N-dimethylamino group and other N,N-di-($C_1$-$C_4$ alkyl)amino groups; sulfo group; and groups each comprising a plurality of these groups combined.

Examples of the aromatic compounds (C) include benzene, toluene, xylenes, mesitylene, ethylbenzene, styrene, phenylacetylene, biphenyl, acetophenone, benzophenone, chlorobenzene, bromobenzene, phenol, anisole, diphenyl ether, phenyl acetate, benzoic acid, phthalic anhydride, phthalimide, methyl benzoate, ethyl benzoate, benzamide, benzonitrile, nitrobenzene, aniline, N,N-dimethylaniline, other benzene and derivatives thereof; naphthalene, azulene, indacene, anthracene, phenanthrene, triphenylene, pyrene and other aromatic hydrocarbons each comprising a plurality of condensed benzene rings, and derivatives thereof such as naphthol, methoxynaphthalene, naphthyl acetate, naphthoquinone and anthraquinone; pyridine, furan, thiophene and other aromatic heterocyclic compounds. Among them, preferred are compounds having hydroxyl group or a substituted oxy group such as an alkoxy group or acyloxy group bonded to their aromatic ring, such as phenol derivatives and naphthol derivatives; and compounds each having an alkyl group bonded to their aromatic ring.

Reaction

The reaction is performed in the presence of, or in the absence of, a solvent. The solvent can be appropriately selected according to the type of the material aromatic compound (C) and other conditions. Examples of the solvent are acetic acid, propionic acid, trifluoroacetic acid, other carboxylic acids, and other organic acids; formamide, acetamide, dimethylformamide (DMF), dimethylacetamide and other amides; nitromethane, nitroethane and other nitro compounds; ethyl acetate, butyl acetate and other esters; acetone, methyl ethyl ketone and other ketones; diethyl ether, diisopropyl ether, dimethoxyethane, tetrahydrofuran, dioxane and other chain or cyclic ethers; ethanol, propanol, butanol, t-butyl alcohol and other alcohols; hexane, octane and other aliphatic hydrocarbons; cyclopentane, cyclohexane, metylcyclohexane and other alicyclic hydrocarbons; chloroform, dichloromethane, dichloroethane, carbon tetrachloride and other halogenated hydrocarbons; water; and mixtures of these solvents. Among them, protic solvents such as organic acids are preferred.

The process of the present invention enables the reaction to smoothly proceed even under relatively mild conditions. A reaction temperature can be appropriately set according to the type(s) of the material compound(s) and other conditions and is generally from about 0° C. to about 200° C., preferably from about 40° C. to about 150° C., and more preferably from about 60° C. to about 120° C. The reaction can be performed at normal atmospheric pressure or under a pressure (under a load). A reaction pressure is, for example, from about 0.1 to about 5 MPa and preferably from about 0.1 to about 2 MPa. The reaction can sufficiently smoothly proceed even at normal atmospheric pressure (0.1 MPa). The reaction can be performed in an atmosphere of or under flow of oxygen and carbon monoxide in a conventional system such as batch system, semi-batch system or continuous system.

According to the process, the oxidative carboxylation of the material aromatic compound (C) proceeds to yield a corresponding aromatic carboxylic acid having one or more carboxyl groups bonded to the aromatic ring of the aromatic compound (C). For example, when the compound represented by Formula (1) is used as the aromatic compound (C), a compound represented by following Formula (2) is formed:

Ar—(COOH)$_m$ (2)

wherein m is an integer of 1 or more; and Ar has the same meaning as defined above.

Under some reaction conditions, an aromatic polycarboxylic acid of Formula (2) wherein m is an integer of 2 or more, such as an aromatic dicarboxylic acid and/or a salt of an aromatic carboxylic acid may be formed in addition to or in lieu of an aromatic monocarboxylic acid of Formula (2) wherein m is 1.

After the completion of the reaction, reaction products can be separated and purified by separation means such as filtration, concentration, distillation, extraction, crystallization, recrystallization, adsorption or column chromatography, or a combination of these separation means.

The present invention will be illustrated in further detail with reference to several examples below, which are not intended to limit the scope of the invention.

EXAMPLE 1

A mixture of 2 mmol of anisole, 0.1 mmol of palladium (II) acetate [Pd(OAc)$_2$], 0.04 mmol of $H_5PMo_{10}V_2O_{40}$ and 7 ml of acetic acid was stirred in a reactor at a constant temperature of 90° C. in an atmosphere of a gaseous mixture of carbon monoxide/oxygen (0.05 MPa/0.05 MPa, total pressure: 0.1 MPa) for 15 hours. The reaction mixture was analyzed by gas chromatography to find that anisic acid (methoxybenzoic acid) was formed in a yield of 79% (ortho-form:para-form=3:7) with a conversion from anisole of 79%.

EXAMPLE 2

The procedure of Example 1 was repeated, except for using 0.04 mmol of $H_7PMo_8V_4O_{40}$ instead of $H_5PMo_{10}V_2O_{40}$. The reaction mixture was analyzed by gas chromatography to find that anisic acid was formed in a yield of 39% (ortho-form:para-form=3:7) with a conversion from anisole of 49%.

EXAMPLE 3

The procedure of Example 1 was repeated, except for using 0.1 mmol of palladium sulfate [$PdSO_4$] instead of palladium(II) acetate. The reaction mixture was analyzed by gas chromatography to find that anisic acid was formed in a yield of 40% (ortho-form:meta-form:para-form=22:2:76) with a conversion from anisole of 78%.

EXAMPLE 4

The procedure of Example 1 was repeated, except for using 106 mg of 10% by weight Pd/C (palladium supported by carbon) instead of palladium(II) acetate. The reaction mixture was analyzed by gas chromatography to find that anisic acid was formed in a yield of 20% (ortho-form:para-form=3:7) with a conversion from anisole of 35%.

EXAMPLE 5

The procedure of Example 1 was repeated, except for using 0.1 mmol of bis(acetylacetonato)palladium(II) [Pd(acac)$_2$] instead of palladium(II) acetate. The reaction mixture was analyzed by gas chromatography to find that anisic acid was formed in a yield of 17% (ortho-form:meta-form:para-form=29:7:64) with a conversion from anisole of 23%.

EXAMPLE 6

The procedure of Example 1 was repeated, except for using 2 mmol of toluene instead of anisole. The reaction mixture was analyzed by gas chromatography to find that toluic acid was formed in a yield of 24% (ortho-form:meta-form:para-form=32:8:60) with a conversion from toluene of 33%.

EXAMPLE 7

The procedure of Example 1 was repeated, except for using 2 mmol of phenyl acetate instead of anisole. The reaction mixture was analyzed by gas chromatography to find that acetoxybenzoic acid was formed in a yield of 20% (ortho-form:para-form=3:7) with a conversion from phenyl acetate of 25%.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A process for producing an aromatic carboxylic acid, comprising the step of reacting an aromatic compound (C) represented by the following formula (1)

$$Ar-H \qquad (1),$$

wherein Ar is an aromatic cyclic group, with carbon monoxide (D) and molecular oxygen (E) in the presence of a palladium compound catalyst (A) and a catalyst (B) to thereby yield an aromatic carboxylic acid corresponding to the aromatic compound (C) except with one or more carboxyl groups bonded to its aromatic ring, the catalyst (B) comprising:

a heteropolyacid or a salt thereof (B1); and/or a mixture of oxo acids and/or salts thereof (B2), the mixture (B2) containing, as a whole, one of P and Si and at least one selected from the group consisting of V, Mo and W.

2. The process according to claim 1, wherein the heteropolyacid or a salt thereof (B1) contains, as its constitutional elements, one of P and Si, and at least one selected from the group consisting of V, Mo and W.

3. The process according to claim 1 or 2, wherein the heteropolyacid or a salt thereof (B1) is a phosphovanadomolybdic acid or phosphomolybdic acid represented by the following formula:

$$A_{3+n}[PMo_{12-n}V_nO_{40}]$$

wherein A represents at least one selected from the group consisting of a hydrogen atom, $NH_4$, an alkali metal and an alkaline earth metal; and n is an integer from 0 to 10, or a salt thereof.

* * * * *